(12) United States Patent
Lewis et al.

(10) Patent No.: US 10,079,871 B2
(45) Date of Patent: Sep. 18, 2018

(54) CUSTOMIZING MEDIA ITEMS FOR PLAYBACK ON ALTERNATIVE PLAYBACK DEVICES PAIRED WITH A USER DEVICE

(71) Applicant: Google LLC, Mountain View, CA (US)

(72) Inventors: Justin Lewis, Marina Del Rey, CA (US); Richard Rapp, Marina Del Ray, CA (US)

(73) Assignee: Google LLC, Mountain View, CA (US)

( * ) Notice: Subject to any disclaimer, the term of this patent is extended or adjusted under 35 U.S.C. 154(b) by 119 days.

(21) Appl. No.: 15/289,886

(22) Filed: Oct. 10, 2016

(65) Prior Publication Data
US 2018/0103079 A1   Apr. 12, 2018

(51) Int. Cl.
| | |
|---|---|
| *G06F 15/16* | (2006.01) |
| *H04L 29/06* | (2006.01) |
| *H04N 21/2387* | (2011.01) |
| *H04N 21/472* | (2011.01) |
| *H04L 29/08* | (2006.01) |
| *H04N 21/84* | (2011.01) |

(52) U.S. Cl.
CPC .......... *H04L 65/604* (2013.01); *H04L 67/146* (2013.01); *H04N 21/2387* (2013.01); *H04N 21/47217* (2013.01); *H04L 67/02* (2013.01); *H04N 21/84* (2013.01)

(58) Field of Classification Search
CPC ..... H04L 65/604; H04L 67/146; H04L 67/02; H04N 21/47217; H04N 21/2387; H04N 21/84
See application file for complete search history.

(56) References Cited

U.S. PATENT DOCUMENTS

| | | | |
|---|---|---|---|
| 9,173,000 B2 | 10/2015 | Clift et al. | |
| 9,792,003 B1 * | 10/2017 | Story, Jr. | ............... G06F 3/0484 |
| 9,942,592 B2 * | 4/2018 | Moon | ................ H04N 21/4122 |
| 2013/0016858 A1 * | 1/2013 | Masaki | ............. H04N 21/4126 |
| | | | 381/104 |
| 2013/0022221 A1 * | 1/2013 | Kallai | ...................... H04R 3/12 |
| | | | 381/300 |
| 2016/0026429 A1 * | 1/2016 | Triplett | ................... G06F 3/165 |
| | | | 715/716 |
| 2016/0094893 A1 * | 3/2016 | Tse | ....................... H04N 21/812 |
| | | | 725/32 |
| 2016/0139868 A1 | 5/2016 | Vedula et al. | |

* cited by examiner

*Primary Examiner* — Michael A Keller
(74) *Attorney, Agent, or Firm* — Foley & Lardner LLP

(57) ABSTRACT

A user device receives a first media item that is associated with a second media item. The device determines that a playback state for the device indicates that the device is paired with an alternative playback device. The device sends the playback state in a request for the second media item, receives the second media item in a first format for playback on the user device and in a second format for playback on the alternative playback device. The device determines whether the playback state of the device is the same. The device displays a first graphical representation of the second media item in the first format on the user device if the user device is no longer paired with the alternative playback device and displays a second graphical representation of the second media item in the second format on the user device if the user device is still paired with the alternative playback device.

15 Claims, 6 Drawing Sheets

CUSTOMIZING MEDIA ITEMS FOR PLAYBACK ON ALTERNATIVE PLAYBACK DEVICES PAIRED WITH A USER DEVICE

TECHNICAL FIELD

The present disclosure relates to a technique for providing content, such as media from a source of such content to a user device or system via a communication network. More particularly, the present disclosure relates to a technique for ensuring that content provided for a user of a user device is compatible with playback on an alternative playback device if the user device is paired with the alternative playback device.

BACKGROUND

Existing systems for provisioning media content (e.g., videos, music) from a server to one or more user devices generally use a protocol for streaming such content from the server to a playback means (i.e., a video and/or audio player) on the user device, as long as such player is capable of receiving such content for display on the device. On typical user devices, applications or players may be available to receive and use/play such content. The user device may be in proximity to an external media streaming device that streams content for presentation on output devices, such as a television and/or a home theater audio system. The user device can display various media content (e.g., videos, music) to a user, and the user may select media content for playback on either the user device or an output device of the media streaming device. In existing systems, the server typically transmits media content (e.g., videos, music) to the user device for playback on the user device. The user device may have a smaller display and a basic speaker system as compared to the output devices (e.g., television and/or a home theater audio system) that are connected to a media streaming device. In existing systems, the media content which the server provides to the user device is generally not customized for the hardware of the output devices of the media streaming device. This is because existing techniques rely on the settings of the user device with no means to determine whether the user device is capable of initiating and/or controlling playback of the media content on output devices of a media streaming device.

Traditionally, when a user device loads a web page that has a placeholder for additional media content (e.g., a recommended video or an advertisement), the user device usually sends a request to a server for the additional media content. The server receives the request, selects the additional media content, and sends the additional media content to the user device. The server is typically unaware of whether the user device is capable of initiating and/or controlling playback of the additional media content on output devices of a media streaming device. The user device loads the additional media content in the web page. With conventional content sharing systems, after the additional media content is loaded, the user device then determines whether the user device can communicate with a media streaming device. If the user device can communicate with a media streaming device, a media player on the user device can display an indicator (e.g., icon) to notify the user that the additional media content item can be played on an output device of the media streaming device.

In existing systems, the server typically provides additional media content pertaining to the user request without knowledge of the user device's capability to initiate and/or control playback of the additional media content on a media streaming device. As such, the server usually provides additional media content that is formatted for playback on the user device, which may not be the best format to use if the additional media content can be played on an output device of a media streaming device such as a television and/or a home theater sound system.

Conversely, the server can provide the user device with additional media content that is formatted for playback on an output device of a media streaming device such as a television and/or a home theater sound system. However, if the user device cannot communicate with the media streaming device, a large amount of broadband data bandwidth and memory may be used for transmitting and playing the additional media content in a format not compatible with the user device.

Further, in existing systems, when additional media content is loaded on a user device and then played on an output device of a media streaming device, content sharing systems typically assign two different sessions for loading the additional media content on the user device and playing the additional media content on the output device of the media streaming device. Conventional content sharing systems generally do not attribute the time the additional media content is played on the output device of the media streaming device with the presentation of the additional media content on the user device, and mistakenly track the displaying of the additional media content on the user device and playing of the additional media content on the output device of the media streaming device independently.

SUMMARY

The following presents a simplified summary of various aspects of this disclosure in order to provide a basic understanding of such aspects. This summary is not an extensive overview of all contemplated aspects, and is intended to neither identify key or critical elements nor delineate the scope of such aspects. Its purpose is to present some concepts of this disclosure in a simplified form as a prelude to the more detailed description that is presented later.

In an aspect of the present disclosure, a processing device of a user device receives a first media item from a server. The first media item is associated with a second media item. The processing device determines that a playback state for the user device indicates that the user device is paired with an alternative playback device, sends a request to the server for the second media item. The request includes the playback state for the user device. The processing device receives, from the server, the second media item in a first format for playing the second media item on the user device and receives the second media item in a second format for playing the second media item on the alternative playback device. The processing device determines whether the playback state of the user device no longer indicates that the user device is paired with the alternative playback device.

Responsive to determining that the playback state of the user device no longer indicates that the user device is paired with the alternative playback device, the processing device displays a first graphical representation of the second media item in the first format on the user device. User selection of the first graphical representation triggers playback of the second media item on the user device. Responsive to determining that the playback state of the user device indicates that the user device is paired with the alternative playback device, the processing device displays a second graphical representation of the second media item in the second format on the user device. User selection of the second graphical representation triggers playback of the second media item on the alternative playback device.

In one implementation, the playback state is stored locally on the user device. In one implementation, the alternative playback device supports at least one of casting technology or mirroring technology. In one implementation, the processing device displays the second graphical representation of the second media item in the second format on the user device, receives user selection of the second graphical representation, and sends a universal resource identifier of the second media item and a tracking identifier associated with a session identifier of the request to the alternative playback device.

In one implementation, the second graphical representation of the second media item in the second format includes a thumbnail, a string placeholder for an identifier of the alternative playback device, and a universal resource identifier for playing the selected candidate media item on the alternative playback device. In one implementation, the processing device displays the second graphical representation of the second media item in the second format on the user device by determining an identifier of the alternative playback device, and displaying the identifier of the alternative playback device in the second graphical representation of the second media item. In one implementation, the second media item is at least one of recommended video, recommended audio, or an advertisement.

In one implementation, the processing device of a server receives a request from a user device for an additional media item pertaining to a first media item to be displayed on the user device, determines, from a playback state for the user device in the request, whether the additional media item is to be played on an alternative playback device. Responsive to a determination that the additional media item is to be played on the alternative playback device, the processing device of the server identifies a set of candidate media items that are designated for playback on the alternative playback device, selects a candidate media item with a highest ranking from the set of candidate media items as the additional media item, and sends a data package to the user device for presenting the selected candidate media item as the additional media item on the user device.

In one implementation, the processing device of the server determines that the playback state indicates that the additional media item is not to be played on the alternative playback device, and excludes the subset of media items that are designated for playback on the alternative playback device from the set of candidate media items. In one implementation, the data package includes a first format for playing the selected candidate media item on the user device, and a second format for playing the selected candidate media item on the alternative playback device. In one implementation, the processing device of the server determines that the playback state indicates that the additional media item is not to be played on the alternative playback device, creates a tracking identifier based on a session identifier that is associated with the request, adds the tracking identifier to a universal resource identifier for playing the selected candidate media item on the alternative playback device, and creates the data package including the universal resource identifier with the tracking identifier.

In one implementation, the processing device of the server receives output device data describing one or more features of one or more output devices connected to the alternative playback device, and selects one or more universal resource identifiers based on the one or more features of one or more output devices connected to the alternative playback device.

An apparatus to customize media items for playback on alternative playback devices paired with a user device is also described. In one implementation, the apparatus includes means for receiving a first media item from a server. The first media item is associated with a second media item. The apparatus includes means for determining that a playback state for the user device indicates that the user device is paired with an alternative playback device, means for sending a request to the server for the second media item. The request includes the playback state for the user device. The apparatus includes means for receiving, from the server, the second media item in a first format for playing the second media item on the user device and means for receiving the second media item in a second format for playing the second media item on the alternative playback device. The apparatus includes means for determining whether the playback state of the user device no longer indicates that the user device is paired with the alternative playback device.

The apparatus includes means for displaying a first graphical representation of the second media item in the first format on the user device responsive to determining that the playback state of the user device no longer indicates that the user device is paired with the alternative playback device. User selection of the first graphical representation triggers playback of the second media item on the user device. The apparatus includes means for displaying a second graphical representation of the second media item in the second format on the user device responsive to determining that the playback state of the user device indicates that the user device is paired with the alternative playback device. User selection of the second graphical representation triggers playback of the second media item on the alternative playback device.

In one implementation, the playback state is stored locally on the user device. In one implementation, the alternative playback device supports at least one of casting technology or mirroring technology. In one implementation, the apparatus includes means for displaying the second graphical representation of the second media item in the second format on the user device, means for receiving user selection of the second graphical representation, and means for sending a universal resource identifier of the second media item and a tracking identifier associated with a session identifier of the request to the alternative playback device.

In one implementation, the second graphical representation of the second media item in the second format includes a thumbnail, a string placeholder for an identifier of the alternative playback device, and a universal resource identifier for playing the selected candidate media item on the alternative playback device. In one implementation, the apparatus includes means for displaying the second graphical representation of the second media item in the second format on the user device by means for determining an identifier of the alternative playback device, and means for displaying the identifier of the alternative playback device in the second graphical representation of the second media item. In one implementation, the second media item is at least one of recommended video, recommended audio, or an advertisement.

In one implementation, the apparatus includes means for receiving a request from a user device for an additional media item pertaining to a first media item to be displayed on the user device, means for determining, from a playback state for the user device in the request, whether the additional media item is to be played on an alternative playback device. The apparatus includes means for identifying a set of candidate media items that are designated for playback on the alternative playback device responsive to a determination that the additional media item is to be played on the alternative playback device. The apparatus includes means for selecting a candidate media item with a highest ranking from the set of candidate media items as the additional media item, and means for sending a data package to the user device for presenting the selected candidate media item as the additional media item on the user device.

In one implementation, the apparatus includes means for determining that the playback state indicates that the additional media item is not to be played on the alternative playback device, and means for excluding the subset of media items that are designated for playback on the alternative playback device from the set of candidate media items. In one implementation, the data package includes a first format for playing the selected candidate media item on the user device, and a second format for playing the selected candidate media item on the alternative playback device. In one implementation, the apparatus includes means for determining that the playback state indicates that the additional media item is not to be played on the alternative playback device, means for creating a tracking identifier based on a session identifier that is associated with the request, means for adding the tracking identifier to a universal resource identifier for playing the selected candidate media item on the alternative playback device, and means for creating the data package including the universal resource identifier with the tracking identifier.

In one implementation, the apparatus includes means for receiving output device data describing one or more features of one or more output devices connected to the alternative playback device, and means for selecting one or more universal resource identifiers based on the one or more features of one or more output devices connected to the alternative playback device.

In additional implementations, computing devices for performing the operations of the above described implementations are also implemented. Additionally, in implementations of the disclosure, a computer readable storage media may store instructions for performing the operations of the implementations described herein.

BRIEF DESCRIPTION OF THE DRAWINGS

Aspects and implementations of the present disclosure will be understood more fully from the detailed description given below and from the accompanying drawings of various aspects and implementations of the disclosure, which, however, should not be taken to limit the disclosure to the specific aspects or implementations, but are for explanation and understanding only.

DETAILED DESCRIPTION

Figure 1:
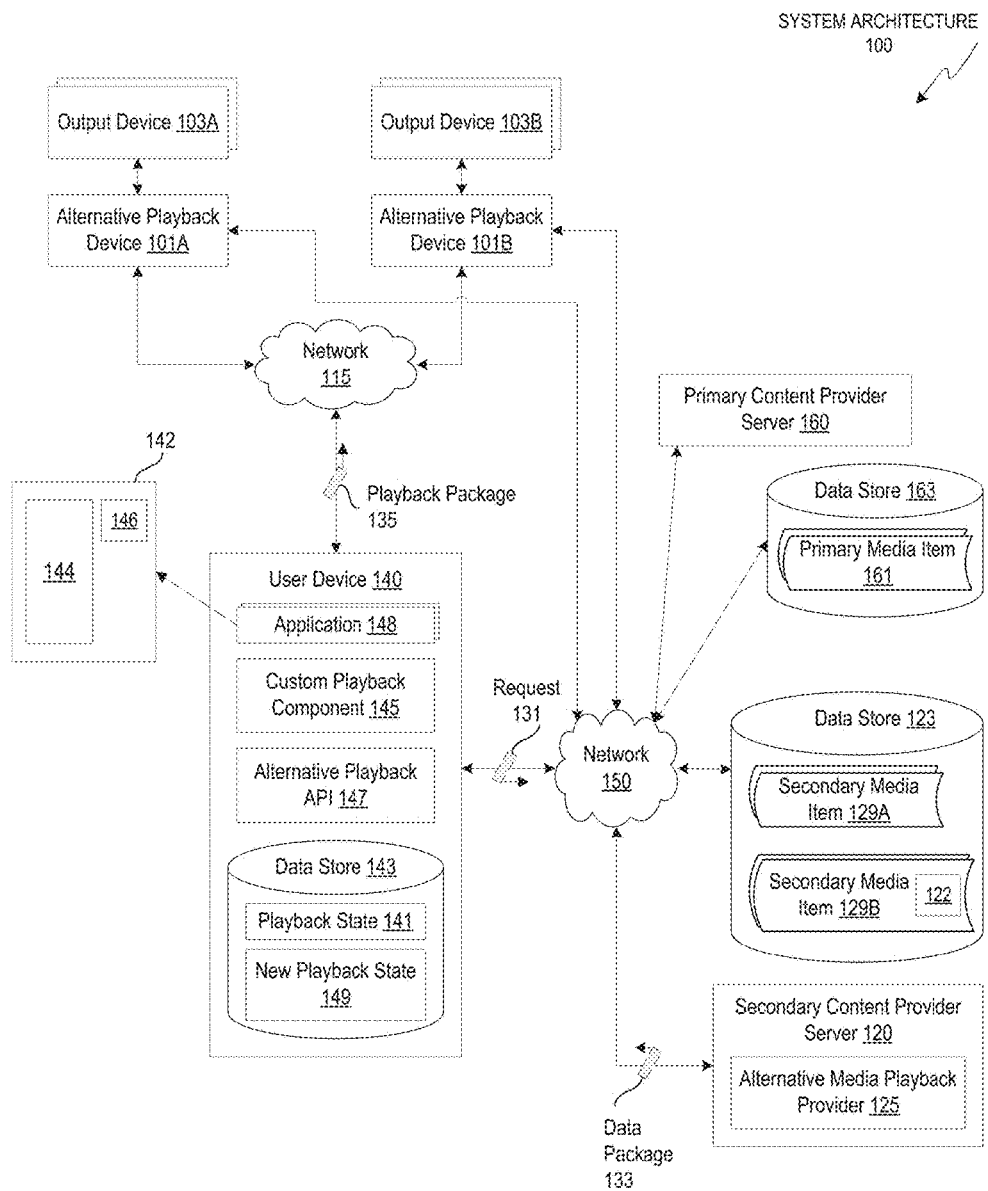
FIG. 1 illustrates an example of system architecture for customizing a media item based on a capability of a user device to control playback of the media item on an alternative playback device, in accordance with one implementation of the disclosure.

Aspects and implementations of the present disclosure provide a mechanism for ensuring that media items are in an appropriate format for playback on hardware of a user device or on hardware associated with alternative playback devices that the user device is paired with. An alternative playback device is a media streaming device that can receive instructions from a user device to play a media item on a display that is separate from the user device. Media items can be, for example, web page content, mobile application ("app") content, digital images, digital audio, and/or digital video. The media items can be primary media items and secondary media items. A primary media item can be, for example, web page content and mobile app content. A secondary media item can be, for example, a recommended video, recommended audio, or an advertisement. A secondary media item is hereinafter also referred to as an additional media item. A primary media item can be associated with one or more secondary media items. For example, the primary media item may be mobile app content and the secondary media item may be a recommended video or an advertisement to be displayed in relation to the mobile app content.

As discussed above, conventional systems are typically unaware of whether a user device is paired with an alternative playback device (e.g., a second screen device in the user's living room) and do not provide content customized for playback on the alternative playback device when it is paired with the user device.

Aspects of the present disclosure address the above and other deficiencies by providing a mechanism for ensuring that an additional media item compatible with playback on an alternative playback device is provided if the user device is paired with the alternative playback device. The user device is considered to be paired with the alternative playback device if the user device can communicate with the alternative playback device and can initiate and/or control playback of content on the alternative playback device.

According to some aspects of the present disclosure, prior to the user device sending a request to the server for the additional media item, the user device determines a playback state of the user device that indicates whether the user device is paired with the alternative playback device. The user device sends its playback state to the server to notify the server of the user device's capability of having the additional media item be played on the alternative playback device. The server receives the playback state and can customize the selection of the additional media item based on the user device's playback state. The server can provide a content package that includes the selected additional media item in a format for playing the additional media item on the user device and in another format for playing the additional media item on the alternative playback device. The user device receives the content package, determines if the playback state has changed, and displays the additional media item in the appropriate format on the user device based on whether the playback state has changed.

Accordingly, aspects and implementations of the present disclosure ensure that the server provides the user device with additional media items that are customized for playback on the alternative playback device and the user device if the user device is paired with the alternative playback device. Aspects of the present disclosure also provide a tracking identifier to link the display of the additional media item on the user device to the playback of the additional media item on the alternative playback device.

The technology disclosed herein is advantageous because it avoids overburdening broadband networks with transmissions of large media files from a server to a user device if the user device is not paired with an alternative playback device. Instead, such media files are only transmitted if the user device is paired with an alternative playback device. In addition, by customizing additional media items for playback on an alternative playback device such as a large television screen (e.g., in a user's living room), the technology disclosed herein enables the user to have a more immersive and interactive viewing experience, and to share this experience with the user's friends and family.

Implementations of the present disclosure often reference videos for simplicity and brevity. However, the teaching of the present disclosure are applied to media items generally and can be applied to various types of content, including for example, video, audio, text, images, program instructions, etc.

FIG. 1 illustrates an example of system architecture 100, in accordance with one implementation of the present disclosure. The system architecture 100 includes one or more user devices (e.g., user device 140), one or more servers (e.g., primary content provider server 160, secondary content provider server 160), one or more alternative playback devices 101A,B, one or more output devices 103A,B, networks (e.g., network 115, network 150), and one or more data stores (e.g., data store 163,123,143).

The content provider servers 120,160 can be coupled to one or more data stores 123,163 that store media items. The primary content provider server 160 can be a web service provider, a digital video provider, a music provider, a social media provider, etc. The secondary content provider server 120 can be, for example, an advertisement server or a recommendation server. The media items can be primary media items 161 and secondary media items 129A,B (additional media items). For brevity and simplicity, one primary media item 162 and one secondary media item (e.g., secondary media item 129A, secondary media item 129B) (additional media item) may be used as examples throughout this document. The primary media items 161 and secondary media items 129A,B may be digital content chosen by a user, digital content made available by a user, digital content uploaded by a user, digital content chosen by a content provider, digital content chosen by a broadcaster, etc. Examples of primary media items 161 and secondary media items 129A,B include, and are not limited to, web page content, mobile app content, digital video, digital movies, digital photos, digital music, website content, social media updates, electronic books (ebooks), electronic magazines, digital newspapers, digital audio books, electronic journals, web blogs, real simple syndication (RSS) feeds, electronic comic books, software applications, etc.

The servers 120,160 may be one or more computing devices (such as a rackmount server, a router computer, a server computer, a personal computer, a mainframe computer, a laptop computer, a tablet computer, a desktop computer, etc.), data stores (e.g., hard disks, memories, databases), networks, software components, and/or hardware components that may be used to provide a user with access to primary media items 161 and secondary media items 129A,B and/or provide the primary media items 161 and secondary media items 129A,B. The servers 120,160 may be a part of a content sharing platform that may allow users to consume, upload, share, search for, approve of ("like"), dislike, and/or comment on primary media items 161 and secondary media items 129A,B. The content sharing platform may also include a website (e.g., a web page) or application (e.g., mobile application) back-end software that may be used to provide a user with access to the primary media items 161 and secondary media items 129A,B.

For brevity and simplicity, an online video (also hereinafter referred to as a video) may be used as an example of a secondary media item 129A,B throughout this document. As used herein, "media," "media item," "online media item," "digital media," "digital media item," "content," and "content item" can include an electronic file that can be executed or loaded using software, firmware or hardware configured to present the digital media item to an entity.

In one example, a primary media item 161 may be a video identified by a user of user device 140 and a secondary media item 129A,B may be a video advertisement or a recommended video selected by the secondary content provider server 120 to be presented before, during or after presenting the primary media item 161 on one or more of the user devices (e.g., user device 140). User devices (e.g., user device 140) may each include computing devices such as personal computers (PCs), laptops, mobile phones, smart phones, tablet computers, netbook computers, network-connected televisions, etc. In some implementations, a user device 140 may also be referred to as a "client device."

The user device 140 can include one or more applications (e.g., application 148) for playing the primary media items 161 and the secondary media items 129A,B. The user device 140 can be a mobile device, such as a smart phone, tablet, electronic reader, etc. The applications can be a web browser, a web application, and native mobile applications (mobile app). A web application or web app is a client-server software application that uses a web browser. The web browser renders web pages ("pages") provided by a server to present user interfaces on the user device 140. A native mobile app is an application for a mobile device that is for a particular operating system (e.g., IOS®, Android®) of the mobile device. The mobile application can provide different screen visualizations that are referred to herein as pages. Each page can be represented by a user interface (UI). The mobile application can include a home page UI that can be presented when a user opens the mobile application on the user device 140. A UI of the application 148 (a mobile app, a web browser or a web app) can include navigation, command, and content UI elements. The UI elements can change from page to page. The application 148 can include a media player (e.g., video player, music player, audio player) for playing a media item on the user device 140. A media player can be embedded in a web page provided to a web browser or in a UI of a mobile app.

The system architecture 100 can include one or more alternative playback devices 101A,B that are coupled to one or more output devices 103A,B. The output devices 103A,B can be displays (e.g., televisions, monitors), audio systems (e.g., high-definition television or home audio system), computer systems (e.g., desktops, laptops, tablets) and virtual reality (VR) systems (e.g., VR headset). Each alternative playback device can be connected to multiple output devices. For example, alternative playback device 101A can be connected to a large screen 3D television and a home surround sound system. An alternative playback device 101A,B can be a digital media player that plays primary media items 161 and secondary media items 129A,B (e.g., audio/video, images) on one or more output devices (e.g., high-definition television or home audio system) by directly streaming the primary media items 161 and secondary media items 129A,B via Wi-Fi (wireless fidelity) from the Internet or a local network (e.g., network 115).

A subset of the secondary media items (e.g., secondary media items 129A) in the data store 123 may be compatible for playback using the computing hardware (e.g., display, speaker) of the user device 140. For example, secondary media items 129A may be formatted for a small display on a smartphone, may have lower video quality (e.g., 240$p$ and 360$p$), and may be in stereo sound.

Another subset of the secondary media items (e.g., secondary media items 129B) in the data store 123 can be designated for playback on alternative playback devices 101A,B based on user (e.g., content provider) input. The content providers can be content owners (e.g., video providers, music providers, advertisers) and can designate which secondary media items (e.g., secondary media items 129B) are for playback on alternative playback devices 101A,B. Each of the designated secondary media items 129B can include an indicator 122 (e.g., bit, flag) to indicate that the respective secondary media item 129B is for playback on alternative playback devices 101A,B, as described in greater detail below in conjunction with FIG. 4.

The subset of secondary media items 129B can be specifically formatted for playback on output devices 103A,B that are coupled to the alternative playback devices 101A,B. For example, the subset of secondary media items 129B can be formatted for a display (e.g., television display, projector screen, computer display) that is larger than the display of the user device 140. In another example, secondary media items 129B may be formatted in high definition (HD) video quality, and may be in a surround sound (e.g., Dolby Digital® surround sound, DTS-HD® surround sound) format. In yet another example, the subset of secondary media items 129B may be formatted in a 3D format for output to, for example, a 3D television display or a VR headset. In still another example, the subset of secondary media items 129B may be longer in length, and/or may have type of content (e.g., action movie trailer content) specifically intended for playback on alternative playback devices 101. The format of the subset of secondary media items 129B, which are designated for playback on alternative playback devices 101A,B, may not be supported by the user device 140. For example, a secondary media item 129B may be a 3D video, which may not be supported by the user device 140.

The user device 140 can be coupled to one or more alternative playback devices 101A,B via, for example, network 115 for playing the secondary media items 129A,B on the alternative playback devices 101A,B. The alternative playback devices 101A,B and the user device 140 can include wireless technology for establishing a connection between the alternative playback devices 101A,B and the user device 140. The wireless communication technology can include peer-to-peer (P2P), Bluetooth®, Whisper®, Wi-Fi® (wireless fidelity), Wi-Fi Direct (Wi-Fi P2P), infrared, ultrasonic or other technology.

The secondary media items 129B can be played on the alternative playback devices 101A,B using casting technology and/or mirroring technology. The user device 140 can include an alternative playback application programming interface (API) 147 for each alternative playback device 101A,B that the user device 140 can connect to. Casting technology and mirroring technology refers to content streaming and playback that involves a first device identifying content (e.g., secondary media item 129B) to be played and a second device providing the playback of the identified content. In casting technology, video encoding of the secondary media item 129B is not performed by the user device 140. The user device 140 can send a universe resource identifier (URI) (e.g., universe resource locator (URL)) for the secondary media item 129B to an alternative playback device (e.g., alternative playback device 101A), and the alternative playback device 101 can use the URI to obtain the secondary media item 129B from the secondary content provider server 120 via an Internet connection over network 150. The alternative playback device 101A receives the secondary media item 129B and streams the secondary media item 129B from the URI directly to one or more output devices 103A (e.g., television, home theater audio system).

In mirroring technology, the user device 140 receives the secondary media item 129B (e.g., video) stream over the Internet and network 150, and repackages the stream as a re-formatted secondary media item 129B stream (e.g., re-formatted video stream) for an alternative playback device 101A. The user device 140 streams the re-formatted stream via a Wi-Fi® router of network 115 to the alternative playback device 101A. The alternative playback device 101A outputs the secondary media item 129B to an output device 101A (e.g., television, home theater audio system).

An application 148 on the user device 140 can load a document 142 (e.g., web page, mobile application UI document) that may include a primary media item (e.g., web page content, mobile app content), and a portion (referred to as a media item placeholder 146) to be populated with a graphical representation for the secondary media item (e.g., secondary media item 129A or secondary media item 129B). The document 142 can include multiple media item placeholders. The placeholder 146 can be associated with code (e.g., JavaScript or an iFrame®) to receive a secondary media item and render the received secondary media item or a graphical representation for the received secondary media item in the placeholder 146 in the document 142. The secondary media item (e.g., secondary media item 129A or secondary media item 129B) for the placeholder 146 can be selected by a secondary content provider server 120. The placeholder 146 can be for a particular type of secondary media item (e.g., video ad, display ad, recommended video, etc.), and can include a tag that indicates to a server (e.g., secondary content provider server 120) what type of secondary media item should be used for the placeholder 146.

The user device 140 can include a custom playback component 145 to send a request 131 to a secondary content provider server 120 for a secondary media item (e.g., secondary media 129A or secondary media 129B) depending on whether the user device 140 is paired with alternative playback devices 101A,B. Prior to sending the request 131 to the secondary content provider server 125, the custom playback component 145 can determine a playback state 141 of the user device 140, which indicates whether the user device 140 is paired with (e.g., capable of initiating/controlling playback of a secondary media item (e.g., advertisement, recommended video, recommended audio) on) alternative playback devices 101A,B. The playback state 141 can be an indication of whether the user device 140 includes an alternative playback application programming interface (API) 147, includes the proper operating system permissions to allow the application 148 to initiate playback of a secondary media item on an alternative playback device (e.g., alternative playback device 101A), and whether the user device 140 can communicate with the alternative playback device 101A, as described in greater detail below in conjunction with FIG. 4.

The playback state 141 may already be stored in a data store 143 of the user device 140. The data store 143 can be a cache in which a playback state 141 was stored when it was most recently determined by the custom playback component 145, as described in greater detail below in conjunction with FIG. 4. For example, the cache can store the playback state 141 that was determined when the application 148 last loaded a document 142. The playback state 141 can be stored as part of application data of a mobile application or as a cookie of a web browser. If there is not already a playback state 141 stored in the data store 143, the custom playback component 145 can determine the playback state 141 for the user device 140, as described in greater detail below in conjunction with FIG. 4.

In one implementation, the custom playback component 145 sends a request 131, which includes the playback state 141, for a secondary media item to a primary content provider server 160, and the primary content provider server 160 requests the secondary media item from the secondary content provider server 120. In another implementation, the custom playback component 145 sends a request 131, with the playback state 141, for a secondary media item directly to the secondary content provider server 120.

An alternative media playback provider 125 on the secondary content provider server 120 can receive the request 131 for a secondary media item and can select a secondary media item (e.g., secondary media item 129A or secondary media item 129B) based on the playback state 141 of the user device 140 in the request 131. The alternative media playback provider 125 can use the playback state 141 to either include or exclude the subset of secondary media items 129B, which are formatted for playback on alternative playback devices 101A,B, in the selection process, as described in greater detail below in conjunction with FIG. 5. The alternative media playback provider 125 can also use the playback state 141 to rank the secondary media items 129A,B based on the playback state 141, as described in greater detail below in conjunction with FIG. 5.

If the playback state 141 in the request 131 indicates that the user device 140 is paired with alternative playback devices 101A,B, the alternative media playback provider 125 can select a secondary media item in the subset of secondary media items 129B that are formatted for alternative playback devices 101A,B, as described in greater detail below in conjunction with FIG. 5. If the playback state 141 indicates that the user device 140 is not paired with alternative playback devices 101A,B, the alternative media playback provider 125 can select a secondary media item in the subset of secondary media items 129A that are not formatted for playback on alternative playback devices 101A,B.

The alternative media playback provider 125 can create a data package 133 that includes the selected secondary media item (e.g., secondary media item 129A or secondary media item 129B). In one implementation, the alternative media playback provider 125 sends the data package 133 to the primary content provider server 160, and the primary content provider server 160 sends the data package 133 to user device 140. In another implementation, the alternative media playback provider 125 directly sends the data package 133 to the user device 140.

If the alternative media playback provider 125 selects one of the subset of secondary media items 129B, which are formatted for playback on alternative playback devices 101A,B, the alternative media playback provider 125 can provide the selected secondary media item 129B in multiple formats. The data package 133 can include the selected secondary media item 129B in a first format for playing the selected secondary media item 129B on the user device 140 and can include the selected secondary media item 129B in a second format for playing the selected secondary media item 129B on an alternative playback device 101A.

When the user device 140 receives the data package 133, the user device 140 may no longer be connected to any alternative playback device, and may no longer have the capability for controlling playback of the selected secondary media item 129B on an alternative playback device. The custom playback component 145 on the user device 140 can select either the first format or the second format in the data package 133 based on whether or not the user device 140 is still paired with (e.g., has the capability of controlling the playback of the selected secondary media item 129B) on an alternative playback device. The custom playback component 145 on the user device 140 can determine a new playback state 149 to determine whether the user device 140 is still capable of controlling the playback of the selected secondary media item 129 on an alternative playback device, as described in greater detail below in conjunction with FIG. 4.

If the user device 140 does not have the capability to initiate/control the playback of the selected secondary media item 129 on an alternative playback device, the custom playback component 145 can select the first format. The first format of the selected secondary media item 129B for playing the secondary media item 129B on the user device 140 can include an image or a thumbnail of the selected secondary media item 129B.

Figure 2:
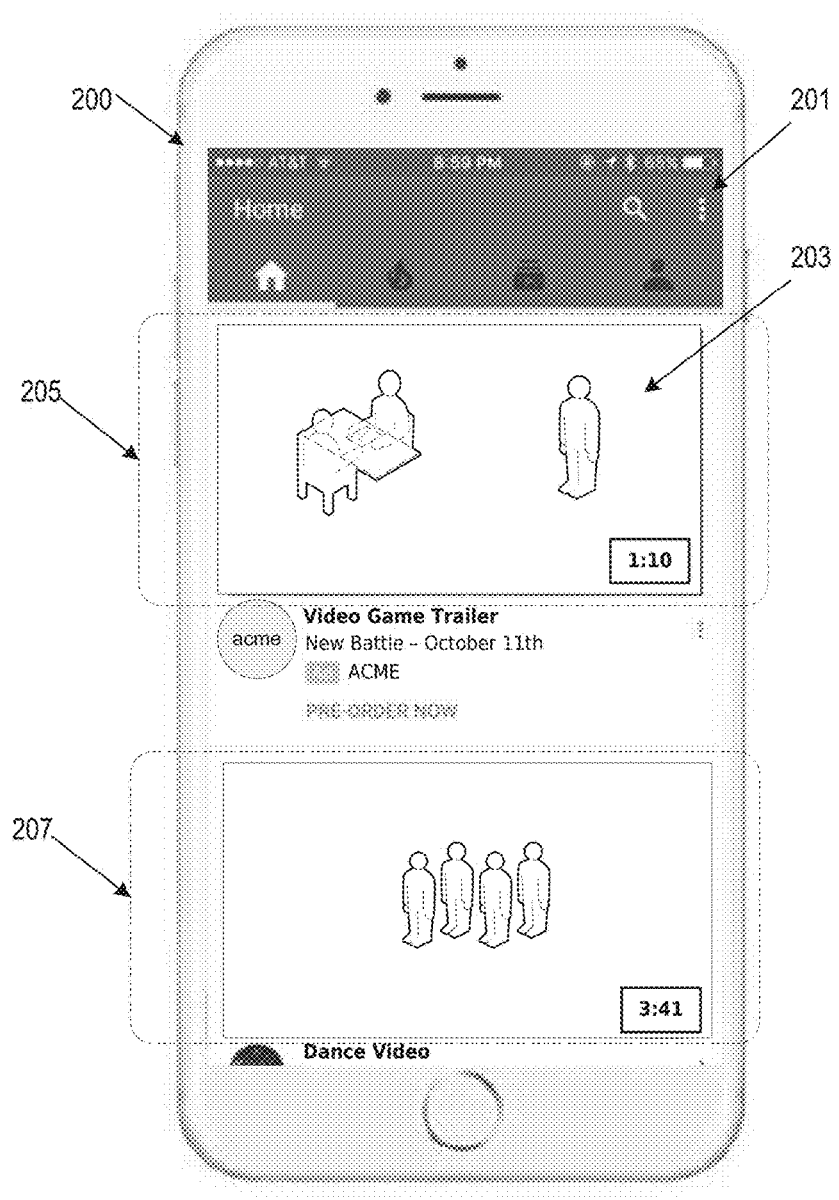
FIG. 2 is an example graphical user interface (GUI) displaying a graphical representation of a media item in a format for playing the media item on a user device, in accordance with an implementation of the disclosure.

FIG. 2 is an example graphical user interface 201 (GUI) displaying a graphical representation of a media item in a format for playing the media item on a user device 200, in accordance with an implementation of the disclosure. The format for playing the secondary media item 205 on the user device 200 can include an image 203 (e.g., thumbnail) of a secondary media item 205. The secondary media item 205 can be an advertisement, recommended video, or recommended audio. For example, the secondary media item 205 may be an advertisement for a new video game. The GUI 201 can display a graphical representation (e.g., thumbnail) for a primary media item 207. The primary media item 207 and/or secondary media item 205 can be a video.

Referring to FIG. 1, if the user device 140 still has the capability to control the playback of the selected secondary media item 129B on an alternative playback device, the custom playback component 145 can select the second format. The second format of the selected secondary media item 129B for playing the selected secondary media item 129B on the alternative playback device 101 can include an image from a frame of the selected secondary media item 129B, an indicator that notifies a user that the selected secondary media item 129B can be played on the alternative playback device 101, a URI for the selected secondary media item 129B, and a tracking identifier. For example, if the selected secondary media item 129B is a video, the second format of the selected secondary media item 129B can be a thumbnail of the selected secondary media item 129B and the indicator can be a message string, such as "Click here to play on your alternative playback device," on the thumbnail. In one implementation, the indicator (e.g., message string) in the second format can be customized for the particular alternative playback devices 101A,B, as described in greater detail below in conjunction with FIG. 4.

Figure 3:
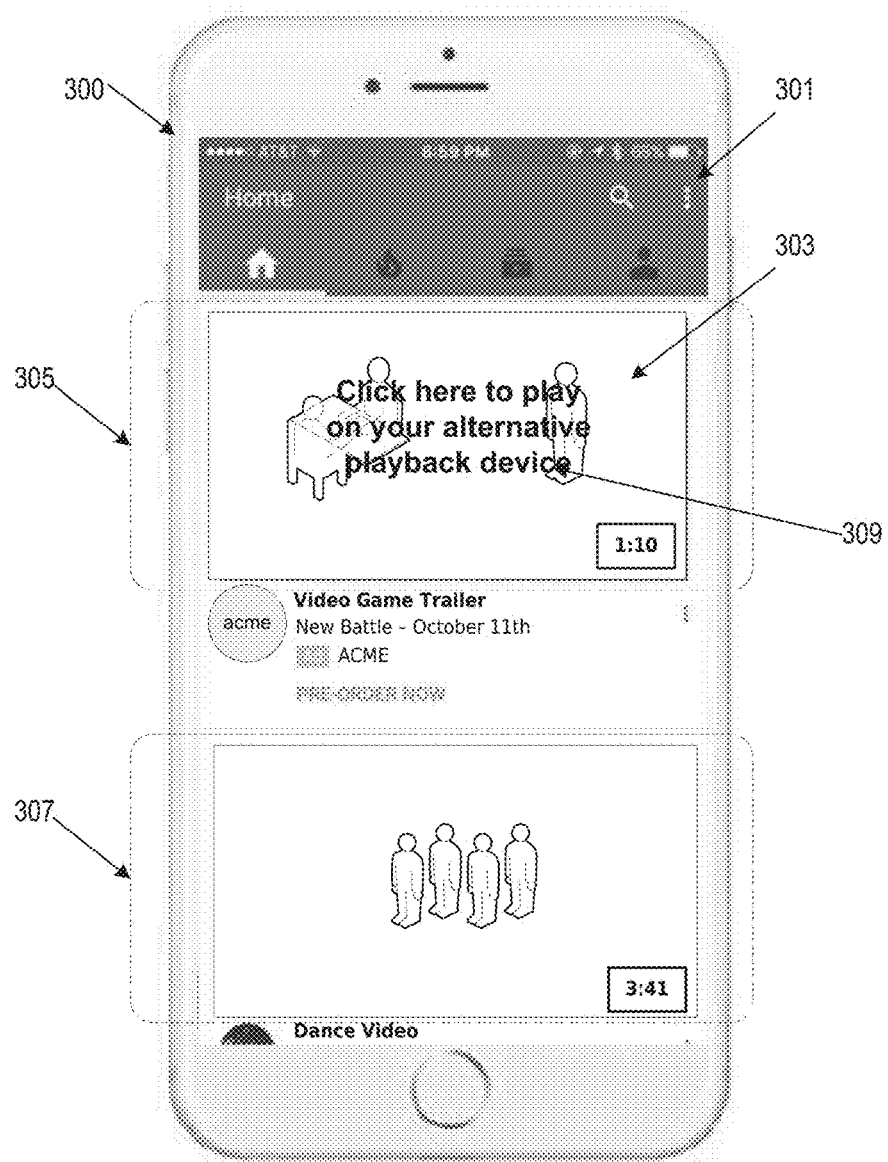
FIG. 3 is an example GUI displaying a graphical representation of a media item on a user device for playing the media item on an alternative playback device, in accordance with an implementation of the disclosure.

FIG. 3 is an example graphical user interface 301 (GUI) displaying a graphical representation of a media item on a user device 300 for playing the media item on an alternative playback device, in accordance with an implementation of the disclosure. The GUI 301 can display a graphical representation (e.g., thumbnail) for a primary media item 307. The GUI 301 can display a graphical representation (e.g., thumbnail) for a secondary media item 305 in a format for playing the secondary media item 305 on an alternative playback device. The secondary media item 305 can be an advertisement, recommended video, or recommended audio. For example, the secondary media item 305 may be an advertisement for a new video game. The primary media item 307 and/or secondary media item 305 can be a video. The format for playing the secondary media item 305 on an alternative playback device can include an image 303 (e.g., thumbnail) from a frame of the secondary media item 305 and an indicator 309 that the secondary media item 305 can be played on the alternative playback device. The indicator 309 can be a string.

Referring to FIG. 1, the tracking identifier can be used to link the session of presenting the selected secondary media item 129B on the user device 140 with the session of playing the selected secondary media item 129B on an alternative playback device, as described in greater detail below in conjunction with FIG. 5.

In general, functions described in one implementation as being performed by the content sharing platform can also be performed on the user device 140 in other implementations, if appropriate. In addition, the functionality attributed to a particular component can be performed by different or multiple components operating together. The content sharing platform and media server 120 can also be accessed as a service provided to other systems or devices through appropriate application programming interfaces, and thus is not limited to use in websites. Although implementations of the disclosure are discussed in terms of a media server and a content sharing platform, implementations may also be generally applied to any type of social network providing digital content and connections between users.

In implementations of the disclosure, a "user" may be represented as a single individual. However, other implementations of the disclosure encompass a "user" being an entity controlled by a set of users and/or an automated source. For example, a set of individual users federated as a community in a social network may be considered a "user."

In situations in which the systems discussed here collect personal information about users, or may make use of personal information, the users may be provided with an opportunity to control whether the content sharing platform collects user information (e.g., information about a user's social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by the content sharing platform.

Data stores 123,143, 163 can be a memory (e.g., random access memory), a drive (e.g., a hard drive, a flash drive), a database system, or another type of component or device capable of storing data. Data stores 123, 143, 163 can include multiple storage components (e.g., multiple drives or multiple databases) that may span multiple computing devices (e.g., multiple server computers).

Figure 4:
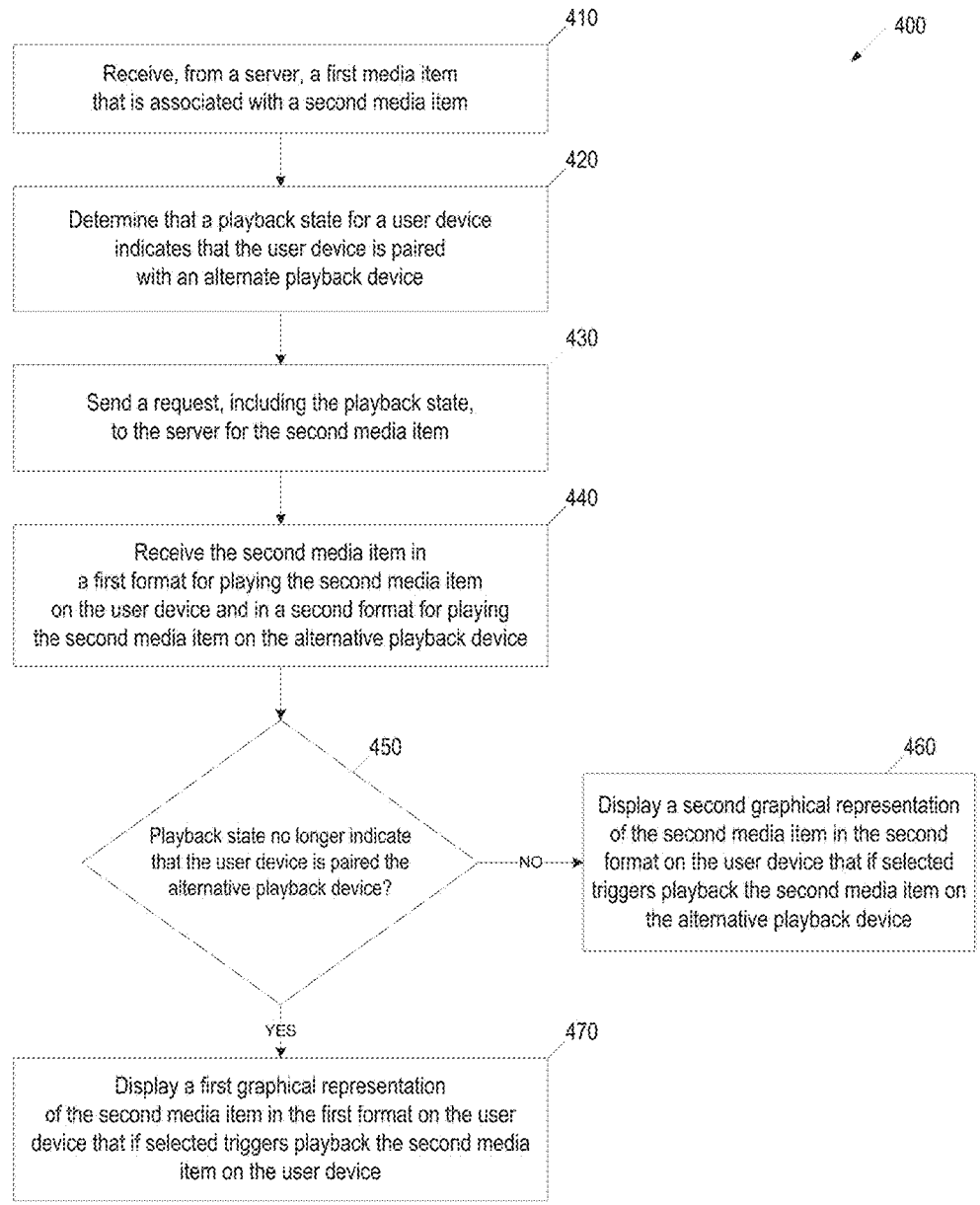
FIG. 4 depicts a flow diagram of a method for providing a custom media item depending on whether a user device is paired with an alternative playback device, in accordance with one implementation of the present disclosure.

FIG. 4 depicts a flow diagram of a method 400 for providing a custom media item depending on whether a user device is paired with an alternative playback device, in accordance with one implementation of the present disclosure. The method 400 is performed by processing logic that may comprise hardware (circuitry, dedicated logic, etc.), software (such as is run on a general purpose computer system or a dedicated machine), or a combination of both. In one implementation, the method is performed by a custom playback component 145 in a user device 140 of FIG. 1, while in some other implementations one or more blocks of FIG. 4 may be performed by another machine. In one implementation, a processing device of a user device (e.g., user device 140 in FIG. 1) performs method 400.

At block 410, the processing device receives a first media item from a server. The first media item is associated with a second media item. The first media item can be, for example, web page content or mobile app content. The second media item can be, for example, video and/or audio, one or more images, etc. The second media item can be an advertisement (e.g., display advertisement, video and/or audio advertisement), a recommended video, a recommended audio, or a recommendation audio/video file. The server can be a secondary content provider server (e.g., secondary content provider server 120 in FIG. 1). The secondary content provider server can be, for example, an advertisement server or a recommendation server. In one example, the first media item may be a video identified by a user of user device and the second media item may be an advertisement selected by the server to be presented before, during, or after presenting the first media item on a user device.

At block 420, the processing device determines that a playback state for the user device indicates that the user device is paired with an alternative playback device. The alternative playback device can be a device that supports casting technology and/or mirroring technology. The processing device can determine whether there is a playback state for the user device that is already stored locally on the user device, and the processing device can access the locally stored playback state. For example, the playback state can be stored as part of application data in a cache of the user device or in a cookie within a browser. The playback state can be represented by a Boolean value. The Boolean value can be a binary variable, having two possible values representing "true" and "false."

The locally stored playback state can represent the playback state of the user device when a previous, most recent, web page was loaded by the browser, or when previous, most recent, mobile application data was loaded by a mobile application. The processing device can examine, for example, cookie data indicating the playback state to determine whether or not the user device, on the previous loading of the web page or application data, was paired with an alternative playback device.

If a playback state for the user device is not yet stored locally on the user device, the processing device can detect whether the user device has alternative playback pairing capability. The processing device can determine the user device capability by checking whether the user device includes any API for any alternative playback device, determining whether the user device operating system has granted the proper permissions for an application (e.g., web browser, mobile app) for initiating/controlling playback of the second media item on the alternative playback device, and whether there is a connection between the user device and the alternative playback device. If the user device does not include an alternative playback API, the processing device can determine that the user device is not capable of being paired with the alternative playback device.

If the user device does include an alternative playback API, the processing device can determine whether the user device operating system (OS) permits an application to initiate/control playback of the second media item on the alternative playback device. If the application does not have the permission(s) from the OS, the processing device can determine that the user device is not capable of being paired with the alternative playback device.

If the application does have the permission(s) from the OS, the processing device can determine whether the user device has a connection with the alternative playback device. The processing device can request the API (e.g., API 147 in FIG. 1) to determine whether an alternative playback device is in proximity of the user device and has established connectivity (e.g., Wi-Fi Direct®, Bluetooth®, Whisper®) with the user device. The processing device can receive a response from the API that indicates whether an alternative playback device is coupled to the user device.

If the user device does not have a connection with the alternative playback device, the processing device can determine that the user device is not capable of being paired with the alternative playback device. If the user device does have a connection with the alternative playback device, the processing device can determine that the user device is capable of being paired with the alternative playback device. The processing device can store a playback state, for example, as a cookie or as application data (e.g., mobile app data) in a cache.

In one implementation, the processing device determines the type of output devices (e.g., output devices 103A,B in FIG. 1) and/or features of the output devices that are coupled to the alternative playback devices, and the processing device includes the playback state and output device data (e.g., types, features) for the connected output devices in the request to the server. Example types of output devices can include televisions, audio systems, VR headsets, and computing devices (e.g., desktops, laptops, tablets, etc.). Example features can include high-definition (HD) display, surround sound, display size, three-dimensional (3D) display, 3D VR, etc.

At block 430, the processing device sends a request to the server for the second media item (e.g., advertisement, recommended video and/or audio). The processing device can send the request upon determining the playback state for the user device. The request can include the playback state for the user device. In one implementation, the playback state is included as cookie data in the request. In one implementation, the request includes output device data that describes the types and/or features of the output devices (e.g., television, sounds system, VR device, HD display, surround sound, 3D display) of the alternative playback device.

At block 440, the processing device receives, from the server, the second media item in a first format for playing the second media item on the user device, and receives the second media item in a second format for playing the second media item on the alternative playback device. The processing device can receive a data package from the server that includes components (e.g., images, strings, URIs, tracking identifiers, etc.) of the second media item in the two formats.

At block 450, the processing device determines whether the playback state of the user device no longer indicates that the user device is paired with the alternative playback device. The processing device can make the determination in response to receiving the second media item in the first format and the second format. The playback state of the user device may change since the time of when the user device sent the request to the server. For example, the user device may lose network connectivity with the alternative playback device.

In one implementation, the processing device requests a local browser, mobile app, or alternative playback device API to make a new determination of whether the playback state of the user device no longer indicates that the user device is paired with the alternative playback device. For example, when the processing device renders the received second media item in a web page in the browser or in a page of a mobile app, the processing device can request the browser, mobile app, or API to refresh the playback state of the user device. The processing device can listen for an update to the playback state for the user device, and can store the updated playback state in a cache. The processing device can receive a new playback state from an application (e.g., web browser, mobile app) or an API. The processing device can replace the playback state in a data store with the new playback state.

When the processing device determines whether the playback state of the user device still indicates that the user device is paired with the alternative playback device, the processing device can also collect metadata pertaining to the alternative playback device. The metadata of the alternative playback device can include an identifier (e.g., name, label) of the alternative playback device.

Each alternative playback device can be assigned a playback device identifier. The playback device identifier can be configurable and/or user-defined. For example, the user device can be in the home of the Smith family and can be coupled to an alternative playback device that is in a living room, and a user (e.g., Smith family member) may assign a name "Smith Living Room Device" to the alternative playback device.

In one implementation, the processing device receives the identifier of each alternative playback device that is coupled to the user device from an application (e.g., web browser, mobile app) or one or more alternative playback APIs. The processing device may use the identifier of the alternative playback device(s) in a graphical representation of the second media item or in a menu, as described in greater detail below.

The processing device can decide which format to use for rendering a graphical representation of the second media item on the user device based on the updated playback state. If the updated playback state of the user device no longer indicates that the user device is paired with the alternative playback device (block 450), the processing device displays a first graphical representation of the second media item in the first format on the user device at block 470. The first graphical representation can include an image and may not include any components (e.g., images, strings, URIs, tracking identifiers, etc.), which may be included in the second format. Selection of the first graphical representation can trigger the playing of the second media item on the user device. If the first graphical representation is selected (e.g., clicked), the second media item can play in a media player in a new tab in the browser, in a media player in a new window of the browser, or in a media player in a mobile app on the user device.

If the updated playback state of the user device still indicates that the user device is paired with the alternative playback device (block 450), the processing device displays a second graphical representation of the second media item in the second format on the user device at block 460. In one implementation, the second format for the second media item includes the identifier of the alternative playback device that is selected for the playback. For example, the second format of the second media item can be a thumbnail of the second media item and an indicator (e.g., message string), such as "Click here to play on the Smith Living Room Device," which can be displayed on the thumbnail.

The user device can be coupled to multiple alternative playback devices. For example, the user device can also be coupled to a second alternative playback device that is in a bedroom room in Smith family home and has an identifier "Smith Bedroom Device." In one implementation, if the user device is connected to multiple alternative playback devices, the second format includes an interstitial user interface (UI) menu (e.g., a pop-up menu) that is to be rendered when a user selects the second graphical representation of the second media item. The UI menu can display the identifiers of the alternative playback devices, and a user can select one of the alternative playback devices for playing the second media item.

The second graphical representation can include a thumbnail of the second media item, which when selected, can trigger the playing of the second media item on the alternative playback device. When the second graphical representation is selected, the processing device sends the URI of the second media item, which is part of the data package received from the server, to the alternate playback device.

In one implementation, when the processing device determines whether the playback state of the user device still indicates that the user device is paired with the alternative playback device at block 450, the processing device can also collect metadata pertaining to the output devices (e.g., output devices 103A,B in FIG. 1). The metadata of the output devices can include the types of the output devices and/or features of the of the output devices. Example types of output devices can include televisions, audio systems, VR headsets, and computing devices (e.g., desktops, laptops, tablets, etc.). Example features can include high-definition (HD) display, surround sound, display size, 3D display, 3D VR, etc.

The processing device can create and/or display an interstitial UI menu (e.g. pop-up menu) that displays the identifiers of the alternative playback devices, and data for the one or more output devices, and a user can select one of the alternative playback devices and one or more output devices for playing the second media item. For example, the pop-up menu may display information that the "Smith Bedroom Device" is connected to a 3D television and that the "Smith Living Room Device" is connected to a VR headset. The data package can include multiple URIs for multiple versions of the second media item that are designated for playback on the alternative playback device. The processing device can select a URI for one of the versions based on the type of output device and/or features of the output device that is to be used for playing the selected secondary media item. For example, the data package can include a first URI for a version of the second media item that supports playback to 3D television, and a second URI for a version of the second media item that supports playback to a VR headset.

The processing device may receive input of the user selection, for example, of the "Smith Living Room Device" is connected to a VR headset, and the processing device can select and send the second URI for the version that is compatible with a VR headset to the alternative playback device. The alternative playback device can use the URI to stream the version of the selected second media item on one or more output devices (e.g., VR headset).

In one implementation, data package includes multiple URIs for multiple versions of the selected second media item that are designated for playback on the alternative playback device. The processing device can select a URI for one of the versions based on the type of output device and/or features of the output device that is to be used for playing the selected secondary media item. For example, the processing device may determine that the selected second media item is to be played on a VR headset, and the processing device can select and send the URI for the version that is compatible with a VR headset to the alternative playback device. The alternative playback device can use the URI to stream the version of the selected second media item on one or more output devices (e.g., VR headset).

The second format can also include a tracking identifier, and the processing device can send the tracking identifier to the alternative playback device. The alternative playback device can use the URI to contact the server to stream the second media item from the server and display the second media item on an output device (e.g., television). For example, the alternative playback device may play the second media item on a big screen television. The alternative playback device can log the time the second media item is played by the alternative playback device on the display with the tracking identifier to associate the time with the second graphical representation that was displayed on the user device. The tracking identifier can be associated with a session identifier for the session when the user device sent the request to the server, as described in greater detail below in conjunction with FIG. 5.

Figure 5:
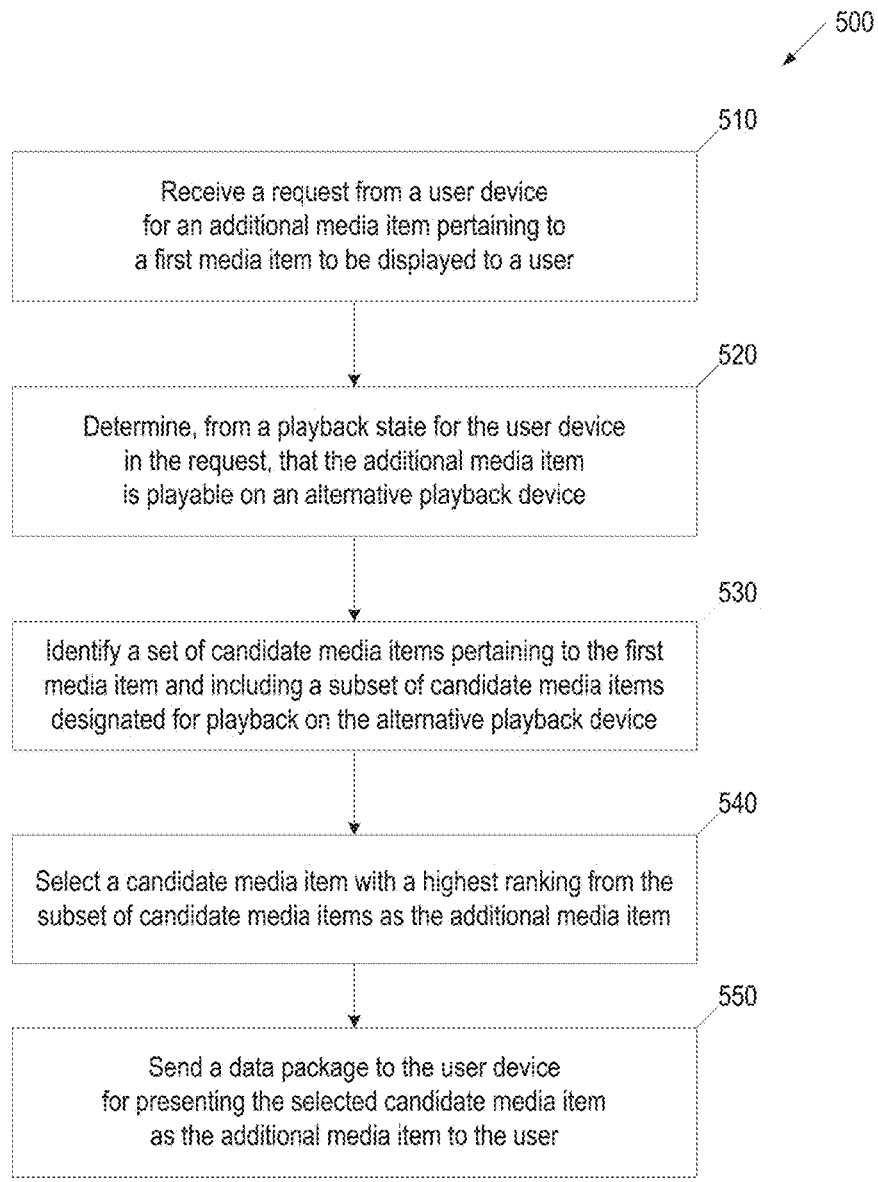
FIG. 5 depicts a flow diagram of a method for selecting a media item based on whether a user device is paired with an alternative playback device, in accordance with one implementation of the present disclosure.

FIG. 5 depicts a flow diagram of a method 500 for selecting a media item based on whether a user device is paired with an alternative playback device, in accordance with one implementation of the present disclosure. The method 500 is performed by processing logic that may comprise hardware (circuitry, dedicated logic, etc.), software (such as is run on a general purpose computer system or a dedicated machine), or a combination of both. In one implementation, the method is performed by an alternative media playback provider 125 in a server 120 of FIG. 1, while in some other implementations one or more blocks of FIG. 5 may be performed by another machine. In one implementation, a processing device of a server computing machine (e.g., secondary content provider server 120 in FIG. 1) performs method 500.

At block 510, the processing device receives a request from a user device for an additional media item pertaining to a first media item to be displayed to a user. The first media item can be, for example, web page content or mobile app content to be displayed on the user device. The additional media item can be an advertisement, a recommended video, or recommended music. The advertisement can be a video or a presentation of a set of images. The video and set of images can include audio.

The request can include a playback state for the user device indicating whether the user device is paired with an alternative playback device. In one implementation, the request includes a tag for a placeholder (e.g., placeholder 146 in FIG. 1) that indicates the type of additional media item that is being requested, as described in greater detail below. In one implementation, the request includes output device data (e.g., types, features) for the output devices that are associated with the alternative playback device(s) that are connected to the user device, as described in greater detail below.

At block 520, the processing device determines, from the playback state for the user device in the request that the additional media item is playable on an alternative playback device. The playback state can be, for example, a state bit or a cookie in the request. Upon receiving the request, the processing device can search for and extract the state bit or cookie in the request to determine whether the user device is paired with an alternative playback device, which indicates whether the additional media item is playable on the alternative playback device. The playback state can be represented by a Boolean value. The Boolean value can be a binary variable, having two possible values representing "true" (e.g., "1") and "false" (e.g., "0"). For example, a "true" value can indicate that the user device is paired with the alternative playback device, which indicates that the additional media item is playable on an alternative playback device and a "false" value can indicate that the additional media item is not playable on an alternative playback device.

At block 530, the processing device identifies a set of candidate media items pertaining to the first media item. The identification can be made in response to a determination that the additional media item is playable on the alternative playback device. The processing device can be coupled to a data store (e.g., data store 123 in FIG. 1) that stores media items. A subset of the media items can be designated for playback on an alternative playback device. The subset of the media items can be specifically formatted for playback on an alternative playback device. For example, the subset of the media items can each be marked with an indicator (e.g., indicator 122 in FIG. 1). The indicator can be a bit or a flag. The bit or a flag can have a Boolean value that is a binary variable, having two possible values representing "true" (e.g., "1") and "false" (e.g., "0"). For example, a "true" value can indicate that the respective media item is specifically formatted for playback on an alternative playback device and a "false" value can indicate that the respective media item is not specifically formatted for playback on an alternative playback device.

If the playback state in the request indicates that the additional media item is not playable on an alternative playback device, the processing device can exclude the subset of candidate media items that are designated for playback on an alternative playback device from the set of candidate media items. If the playback state indicates that the additional media item is playable on an alternative playback device, the processing device can include the subset of candidate media items that are designated for playback on an alternative playback device in the set of candidate media items.

At block 540, the processing device selects a candidate media item with a highest ranking from the subset of candidate media items as the additional media item. The processing device can identify rankings for the set of candidate media items. The rankings can be based on quality scores of candidate media items.

The processing device can identify a quality score of each candidate media item. The quality score is a metric that represents how relevant the respective candidate media item is to a document (e.g., a web page or a mobile application UI document 142 in FIG. 1) and/or to a user that is requesting the document. The components of a quality score can include, for example, CTR (click-through rate), relevance, and landing page. In one example, the CTR for a candidate media item is the ratio of users who click on a specific link to the number of total users who view the candidate media item. In another example, the CTR for a candidate media item that is a video is counted when the video starts playing. A landing page is a standalone web page or mobile app page that is distinct from the main website or the main mobile app and has been designed for a single focused objective to persuade a user to click through to another page.

A ranking for a candidate media item can be an overall score for the respective candidate media item. The ranking (e.g., overall score) can be a function of a quality score and a bid. In one implementation, the ranking for a candidate media item is the quality score of the candidate media item multiplied by the bid of the candidate media item. Each candidate media item can be assigned a bid, which is the highest amount or currency that a content provider is willing to pay when a user selects (e.g., clicks) a graphical representation of the candidate media item. A bid can be user (e.g., content provider, advertiser) defined. The quality score can be generated by the server (e.g., secondary content provider server 120 in FIG. 1), such as an advertisement server or a recommendation server.

The processing device can improve rankings of the subset of candidate media items that are designated for playback on an alternative playback device by modifying (e.g., increasing) the quality scores of the subset of the candidate media items that are designated for playback on an alternative playback device. In one implementation, each quality score is increased by a multiplier or by adding a value to the respective quality score. The multiplier and value can be configurable and user (e.g., system administrator) defined. The increased quality scores can produce higher rankings (e.g., overall scores) for each of the subset of the media items that are marked for playback on an alternative playback device.

The processing device selects a candidate media item with a highest ranking (e.g., overall score) from the subset of candidate media items as the additional media item. At block 550, the processing device sends a data package to the user device for presenting the selected candidate media item as the additional media item to the user. If the playback state in the request indicates that the additional media item can be played on an alternative playback device, the processing device can create the selected candidate media item in multiple formats. The data package can include the selected candidate media item in a first format for playing the additional media item on the user device and the selected candidate media item in a second format for playing the additional media item on the alternative playback device.

In one implementation, there is a tag in the request received at block 510. The tag can indicate the type of additional media item that is being requested. Example types of media items can include text, image, rich media, or video. The video type can include video, an animated set of images, a music file, or any type of media that can be played in a video player, music player, or alternative playback device.

In one implementation, there is a user device identifier in the request received at block 510 that specifies the type (e.g., smartphone, tablet, e-reader, laptop, desktop) of user device. The processing device can use the tag and/or user device identifier to select a first set of components for the first format for playing the additional media item on the user device. For example, if the tag specifies video as the type and the user device identifier specifies a smartphone, the first set of components can include a media file (e.g., video file, music file, presentation file, etc.) of a particular version of the selected candidate media item that is formatted for a smartphone.

A data store (e.g., data store 123 in FIG. 1) can store multiple versions of a media item. For example, the data store can store a version of the media item that is formatted for playback on a mobile device (e.g., smartphone). The first format for a particular user device (e.g., mobile device) can include particular video quality, sound quality, display size, length of the video, and content of the video. For example, the data store can store a video file for a media item that is formatted for a small display on a smartphone, may have lower video quality (e.g., 240$p$ and 360$p$), may be in stereo sound, and may be short in length (e.g., less than 10 seconds). The first format for playing an additional media item on a user device can be configurable and user (e.g., content owner, advertiser) defined.

The second format for playing the additional media item on the alternative playback device can include components that are different from the first format. In one implementation, the request received at block 510 also includes output device data (e.g., types, features) for the output devices that are associated with the alternative playback device(s) that are connected to the user device. Example types of output devices can include televisions, audio systems, VR headsets, and computing devices (e.g., desktops, laptops, tablets, etc.). Example features can include high-definition (HD) display, surround sound, display size, three-dimensional (3D) display, 3D VR, etc.

The processing device can use the tag and/or output device data to select a second set of components for the second format for playing the additional media item on the alternative playback device. The second set of components can include a thumbnail image, one or more strings, one or more URIs for the selected candidate media item, and a tracking identifier. For example, if the tag specifies video as the type and the output device data specifies a 3D television, the second set of components can include a URI of a media file (e.g., video file, music file, presentation file, etc.) of a particular version of the selected candidate media item that is formatted for 3D display. The output device data can specify multiple output devices and the second set of components can include multiple URIs for multiple versions of the selected candidate media item. For example, the output device data may specifies a 3D television and a VR headset, the second set of components can include a first URI of a media file that is formatted for 3D display and a second URI of a media file that is formatted for a VR headset.

The second format for playback on an alternative playback device can include particular video quality, sound quality, display size, length of the media item, and content of the media item. For example, content providers (e.g., content owners, advertisers) can provide a video file for a media item that is formatted for a large (as defined by the content provider) display, a HD display, a panoramic display, and/or a 3D display. For example, the video file may have high video quality (e.g., 720p and 1080p). In another example, the video file may be in surround sound, may be longer (e.g., 30 seconds) in length, and may contain content (e.g., action movie trailer) that is designated for playback on an alternative playback device. The second format for playing an additional media item on an alternative playback device can be configurable and user (e.g., content owner, advertiser) defined.

If the playback state in the request indicates that the additional media item can be played on an alternative playback device, the processing device can create a tracking identifier for the additional media item. The tracking identifier can be derived from a session identifier of the session that is associated with the request. The processing device can add the tracking identifier to one or more URIs of the selected candidate media item, and can include the one or more URIs with the tracking identifier in the data package.

When the alternative playback device plays the additional media item, the alternative playback device can log the consumption (e.g., play) time with the tracking identifier. The tracking identifier can associate the consumption (e.g., play) time of playing the additional media item on the alternative playback device to the graphical representation of the additional media item on the user device.

Figure 6:
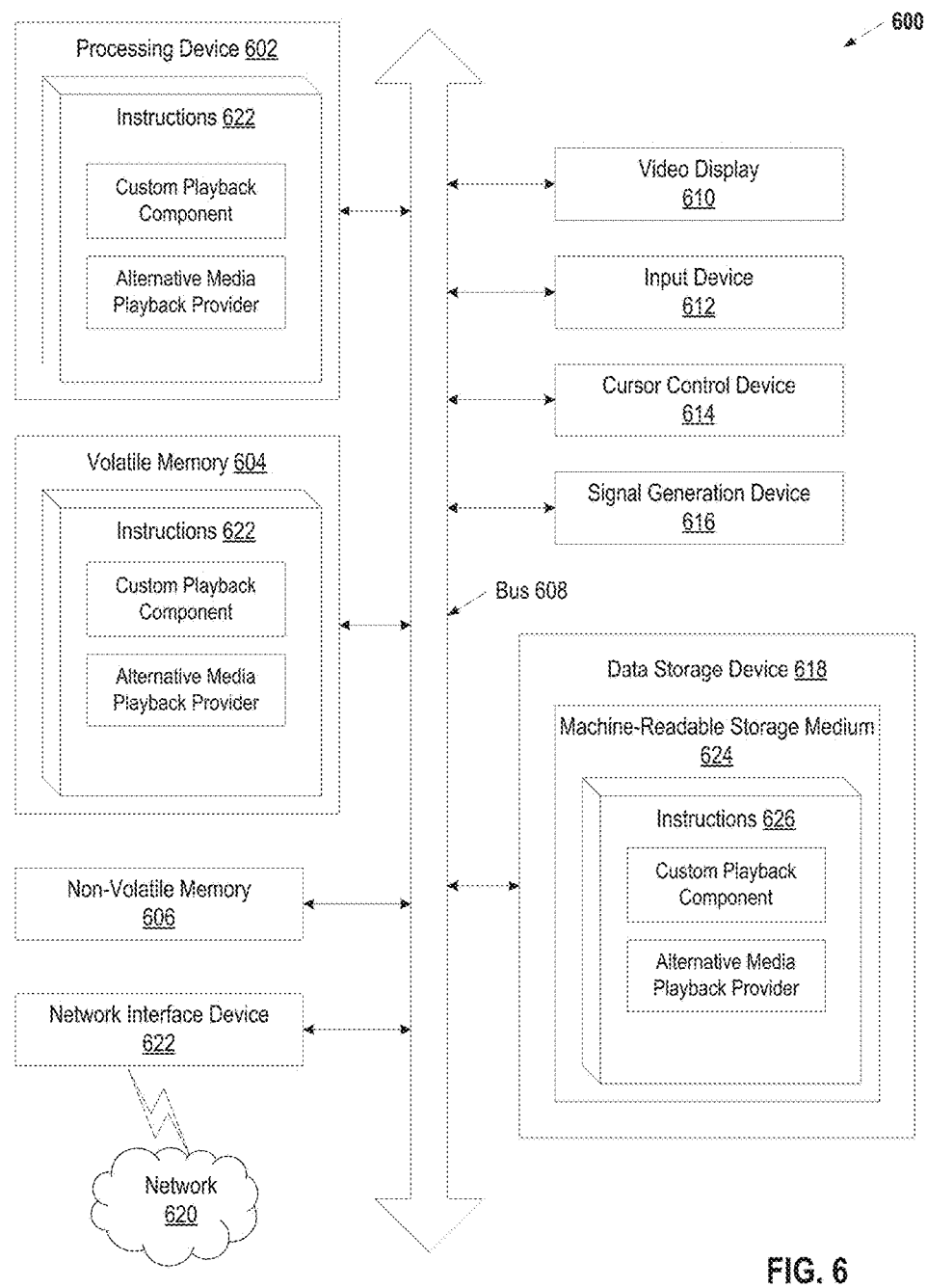
FIG. 6 depicts a block diagram of an example computing device operating in accordance with one or more aspects of the present disclosure.

FIG. 6 depicts a block diagram of a computer system operating in accordance with one or more aspects of the present disclosure. In certain implementations, computer system 600 may be connected (e.g., via a network, such as a Local Area Network (LAN), an intranet, an extranet, or the Internet) to other computer systems. Computer system 600 may operate in the capacity of a user device. Computer system 600 may operate in the capacity of a server or a client computer in a client-server environment. Computer system 600 may be provided by a personal computer (PC), a tablet PC, a set-top box (STB), a Personal Digital Assistant (PDA), a cellular telephone, a web appliance, a server, a network router, switch or bridge, or any device capable of executing a set of instructions (sequential or otherwise) that specify actions to be taken by that device. Further, the term "computer" shall include any collection of computers that individually or jointly execute a set (or multiple sets) of instructions to perform any one or more of the methods described herein.

In a further aspect, the computer system 600 may include a processing device 602, a volatile memory 604 (e.g., random access memory (RAM)), a non-volatile memory 606 (e.g., read-only memory (ROM) or electrically-erasable programmable ROM (EEPROM)), and a data storage device 618, which may communicate with each other via a bus 608.

Processing device 602 may be provided by one or more processors such as a general purpose processor (such as, for example, a complex instruction set computing (CISC) microprocessor, a reduced instruction set computing (RISC) microprocessor, a very long instruction word (VLIW) microprocessor, a microprocessor implementing other types of instruction sets, or a microprocessor implementing a combination of types of instruction sets) or a specialized processor (such as, for example, an application specific integrated circuit (ASIC), a field programmable gate array (FPGA), a digital signal processor (DSP), or a network processor).

Computer system 600 may further include a network interface device 622. Computer system 600 also may include a video display unit 610 (e.g., an LCD), an input device 612 (e.g., a keyboard, an alphanumeric keyboard, a motion sensing input device, touch screen), a cursor control device 614 (e.g., a mouse), and a signal generation device 616.

Data storage device 618 may include a non-transitory machine-readable storage medium 624 on which may store instructions 626 encoding any one or more of the methods or functions described herein, including instructions encoding components of server 120,160 of FIG. 1 for implementing method 500, and/or components of user device 140 of FIG. 1 for implementing method 400.

Instructions 626 may also reside, completely or partially, within volatile memory 604 and/or within processing device 602 during execution thereof by computer system 600, hence, volatile memory 604 and processing device 602 may also constitute machine-readable storage media.

While machine-readable storage medium 624 is shown in the illustrative examples as a single medium, the term "computer-readable storage medium" shall include a single medium or multiple media (e.g., a centralized or distributed database, and/or associated caches and servers) that store the one or more sets of executable instructions. The term "computer-readable storage medium" shall also include any tangible medium that is capable of storing or encoding a set of instructions for execution by a computer that cause the computer to perform any one or more of the methods described herein. The term "computer-readable storage medium" shall include, but not be limited to, solid-state memories, optical media, and magnetic media.

The methods, components, and features described herein may be implemented by discrete hardware components or may be integrated in the functionality of other hardware components such as ASICS, FPGAs, DSPs or similar devices. In addition, the methods, components, and features may be implemented by firmware modules or functional circuitry within hardware devices. Further, the methods, components, and features may be implemented in any combination of hardware devices and computer program components, or in computer programs.

Unless specifically stated otherwise, terms such as "receiving," "determining," "sending," "displaying," "identifying," "selecting," "excluding," "creating," "adding," or the like, refer to actions and processes performed or implemented by computer systems that manipulates and transforms data represented as physical (electronic) quantities within the computer system registers and memories into other data similarly represented as physical quantities within the computer system memories or registers or other such information storage, transmission or display devices. Also, the terms "first," "second," "third," "fourth," etc. as used herein are meant as labels to distinguish among different elements and may not have an ordinal meaning according to their numerical designation.

Examples described herein also relate to an apparatus for performing the methods described herein. This apparatus may be specially constructed for performing the methods described herein, or it may comprise a general purpose computer system selectively programmed by a computer program stored in the computer system. Such a computer program may be stored in a computer-readable tangible storage medium.

The methods and illustrative examples described herein are not inherently related to any particular computer or other apparatus. Various general purpose systems may be used in accordance with the teachings described herein, or it may prove convenient to construct more specialized apparatus to perform methods 400 and 500 and/or each of its individual functions, routines, subroutines, or operations. Examples of the structure for a variety of these systems are set forth in the description above.

The above description is intended to be illustrative, and not restrictive. Although the present disclosure has been described with references to specific illustrative examples and implementations, it will be recognized that the present disclosure is not limited to the examples and implementations described. The scope of the disclosure should be determined with reference to the following claims, along with the full scope of equivalents to which the claims are entitled.

What is claimed is:

1. A method comprising:
receiving a first media item from a server, the first media item being associated with a second media item;
determining, by a processor of a user device, that a playback state for the user device indicates that the user device is paired with an alternative playback device;
sending a request to the server for the second media item, the request comprising the playback state for the user device;
receiving, from the server, the second media item in a first format for playing the second media item on the user device and receiving the second media item in a second format for playing the second media item on the alternative playback device;
determining whether the playback state of the user device no longer indicates that the user device is paired with the alternative playback device;
responsive to determining that the playback state of the user device no longer indicates that the user device is paired with the alternative playback device, displaying a first graphical representation of the second media item in the first format on the user device, wherein user selection of the first graphical representation triggers playback of the second media item on the user device, and
responsive to determining that the playback state of the user device indicates that the user device is paired with the alternative playback device, displaying a second graphical representation of the second media item in the second format on the user device, wherein user selection of the second graphical representation triggers playback of the second media item on the alternative playback device.

2. The method of claim 1, wherein the playback state is stored locally on the user device.

3. The method of claim 1, wherein the alternative playback device supports at least one of casting technology or mirroring technology.

4. The method of claim 1, further comprising:
displaying the second graphical representation of the second media item in the second format on the user device;
receiving user selection of the second graphical representation;
sending a universal resource identifier of the second media item and a tracking identifier associated with a session identifier of the request to the alternative playback device.

5. The method of claim 1, wherein the second graphical representation of the second media item in the second format comprises a thumbnail, a string placeholder for an identifier of the alternative playback device, and a universal resource identifier for playing the selected candidate media item on the alternative playback device.

6. The method of claim 1, wherein displaying the second graphical representation of the second media item in the second format on the user device comprises:
determining an identifier of the alternative playback device; and
displaying the identifier of the alternative playback device in the second graphical representation of the second media item.

7. The method of claim 1, wherein the second media item is at least one of recommended video, recommended audio, or an advertisement.

8. A non-transitory computer readable medium having instructions stored thereon that, when executed by a processing device, cause the processing device to perform operations comprising:
receiving a first media item from a server, the first media item being associated with a second media item;
determining, by the processor of a user device, that a playback state for the user device indicates that the user device is paired with an alternative playback device;
sending a request to the server for the second media item, the request comprising the playback state for the user device;
receiving, from the server, the second media item in a first format for playing the second media item on the user device and receiving the second media item in a second format for playing the second media item on the alternative playback device;
determining whether the playback state of the user device no longer indicates that the user device is paired with the alternative playback device; and
responsive to determining that the playback state of the user device no longer indicates that the user device is paired with the alternative playback device, displaying a first graphical representation of the second media item in the first format on the user device, wherein user selection of the first graphical representation triggers playback of the second media item on the user device, and
responsive to determining that the playback state of the user device indicates that the user device is paired with the alternative playback device, displaying a second graphical representation of the second media item in the second format on the user device, wherein user selection of the second graphical representation triggers playing the second media item on the alternative playback device.

9. The non-transitory computer readable medium of claim 8, wherein the playback state is stored locally on the user device.

10. The non-transitory computer readable medium of claim 8, wherein the alternative playback device supports at least one of casting technology or mirroring technology.

11. The non-transitory computer readable medium of claim 8, the operations further comprising:
displaying the second graphical representation of the second media item in the second format on the user device;
receiving user selection of the second graphical representation;
sending a universal resource identifier of the second media item and a tracking identifier associated with a session identifier of the request to the alternative playback device.

12. The non-transitory computer readable medium of claim 8, wherein the second graphical representation of the second media item in the second format comprises a thumbnail, a string placeholder for an identifier of the alternative playback device, and a universal resource identifier for playing the selected candidate media item on the alternative playback device.

13. The non-transitory computer readable medium of claim 8, wherein displaying the second graphical representation of the second media item in the second format on the user device comprises:
determining an identifier of the alternative playback device; and
displaying the identifier of the alternative playback device in the second graphical representation of the second media item.

14. The non-transitory computer readable medium of claim 8, wherein the second media item is at least one of recommended video, recommended audio, or an advertisement.

15. A system comprising:
a memory; and
a processing device, coupled to the memory, to:
receive a first media item from a server, the first media item being associated with a second media item;
determine that a playback state for the user device indicates that the user device is paired with an alternative playback device;
send a request to the server for the second media item, the request comprising the playback state for the user device;
receive, from the server, the second media item in a first format for playing the second media item on the user device and receiving the second media item in a second format for playing the second media item on the alternative playback device;
determine whether the playback state of the user device no longer indicates that the user device is paired with the alternative playback device;
responsive to determining that the playback state of the user device no longer indicates that the user device is paired with the alternative playback device, display a first graphical representation of the second media item in the first format on the user device, wherein user selection of the first graphical representation triggers playback of the second media item on the user device, and
responsive to determining that the playback state of the user device indicates that the user device is paired with the alternative playback device, display a second graphical representation of the second media item in the second format on the user device, wherein user selection of the second graphical representation triggers playback of the second media item on the alternative playback device.

* * * * *